US012734257B2

(12) United States Patent
Valentini

(10) Patent No.: US 12,734,257 B2
(45) **Date of Patent: *Sep. 15, 2026**

(54) THERAGNOSTIC METHOD FOR CANCER PATIENTS

(71) Applicant: Serena Valentini, Macerata (IT)

(72) Inventor: Serena Valentini, Macerata (IT)

(*) Notice: Subject to any disclaimer, the term of this patent is extended or adjusted under 35 U.S.C. 154(b) by 0 days.

This patent is subject to a terminal disclaimer.

(21) Appl. No.: 18/842,093

(22) PCT Filed: Mar. 3, 2023

(86) PCT No.: PCT/EP2023/055493

§ 371 (c)(1),
(2) Date: Aug. 28, 2024

(87) PCT Pub. No.: WO2023/166205

PCT Pub. Date: Sep. 7, 2023

(65) Prior Publication Data

US 2025/0108135 A1 Apr. 3, 2025

Related U.S. Application Data

(63) Continuation of application No. 17/685,406, filed on Mar. 3, 2022.

(51) Int. Cl.
*A61K 9/00* (2006.01)
*A61K 51/02* (2006.01)
(Continued)

(52) U.S. Cl.
CPC .......... *A61K 51/025* (2013.01); *A61K 9/0019* (2013.01); *A61K 51/121* (2013.01); (Continued)

(58) Field of Classification Search
CPC .................................................... A61K 51/025
See application file for complete search history.

(56) References Cited

FOREIGN PATENT DOCUMENTS

| | | | |
|---|---|---|---|
| EP | 3071241 | B1 | 9/2019 |
| WO | 2021058549 | A1 | 4/2021 |
| WO | 2021225760 | A1 | 11/2021 |

OTHER PUBLICATIONS

Boschi, The emerging role of copper-64 radiopharmaceuticals as cancer theranostics; Drug Discovery Today, vol. 23, No. 8, 2018 (Year: 2018).*

(Continued)

*Primary Examiner* — Paul W Dickinson
(74) *Attorney, Agent, or Firm* — Silvia Salvadori, P.C.; Silvia Salvadori

(57) ABSTRACT

A radiopharmaceutical composition is here described comprising as the active ingredient copper-64 in ionic form (64Cu++), in combination with suitable excipients, and/or diluents, having radioconcentration comprised between 50 and 3,500 MBq/mL at calibration time. Such radiopharmaceutical composition is useful in a method for treating a subject affected by a neoplasia. Such method may comprise a step for evaluating the eligibility of a patient for the treatment, in which 64Cu++ cellular uptake is detected. In case no uptake is detectable, the treatment is not advisable. In case radioactive copper uptake from cancer lesions is detectable, this has a predictive value of response to treatment and the subject is selected for the treatment. If the patient is eligible for the treatment and is selected for the treatment, the method further comprises a step of treating cancer in said subject by administering a therapeutically effective amount of the same 64Cu++ salt.

23 Claims, 4 Drawing Sheets

(51) Int. Cl.
*A61K 51/12* (2006.01)
*A61P 35/00* (2006.01)
*G01N 33/60* (2006.01)
*G01N 33/84* (2006.01)

(52) U.S. Cl.
CPC ............. *A61P 35/00* (2018.01); *G01N 33/60* (2013.01); *G01N 33/84* (2013.01)

(56) References Cited

OTHER PUBLICATIONS

European Medicine Agency (EMA): "Cuprymina: EPAR—Product Information", Sep. 3, 2012, Retrieved from the Internet on Jan. 15, 2015 at URL:http://www.ema.europa.eu/docs/en_GB/document_library/EPAR_-_Product_Information/human/002136/WC500131689.pdf, p. 1-p. 3.
Qin C et al., "Theranostics of malignant melanoma with 64cucL2", The Journal of Nuclear Medicine, Society of Nuclear Medicine, vol. 55, No. 5, May 2, 2014, pp. 812-817, and Qin C et al., "Theranostics of malignant melanoma with 64cucL2", The Journal of Nuclear Medicine, Society of Nuclear Medicine, vol. 55, No. 5, May 2, 2014, retrieved from the Internet on May 24, 2023 at URL: https://jnm.snmjournals.org/highwire/filestream/94621/field_highwire_adjunct_files/0/133850_Supplemental_Data.pdg p. 1.
Gutfilen B et al., "Copper-64: a real theranostic agent", Drug Design, Development and Therapy, vol. 12, Oct. 2, 2018, pp. 3235-3245.
Lewis J et al, "An imaging comparisong of 64 Cu-ATSM and 60 Cu-ATSM in cancer of the uterine cervix", The Journal of Nuclear Medicine, vol. 49, No. 7, Jul. 27, 2008.
Ballinger J. R., Theranostics and precision medicine special feature: Review article: Theranostic radiopharmaceuticals: established agent in current use, Br. J. Radiol 2018 91. pp. 1-8.
Cai H et al., "Reduced 64 CU uptake and tumor growth inhibition by knockdown of human copper transporter 1 in xenograft mouse model of prostate cancer", J. Nucl Med Apr. 2014; 55(4): 622-628.
Capasso E. et al., "Role of 64CUCl2 Pet/Ct in staging of prostate cancer", Ann. Nucl Med Apr. 2, 2015, pp. 1-7.
Catalogna G. et al., "The SGK1 kinase inhibitor SI113 sensitizes theranostic effects of the 64 CuCl2 in human glioblastoma multiforme cells", Cell Physiol Biochem 2017; 43:108-119.
Dos Santos J C et al., "Development of novel PSMA ligands for imaging and therapy with copper isotopes", J Nuci Me 2020 61:70-79.
European Medicine Agency (emea) "Cuprymina: EPAR—Product Information", Sep. 3, 2012.
European Medicine Agency (emea): Cuprymina: EPAR—product information, Sep. 3, 2012, pp. 1-3.
Ferrari C. et al., "Copper-64 dichloride as theranostic agent for glioblastoma multifome: a preclinical study", Biomed Research International, vol. 2015, pp. 1-6.
Fisher G.L. et al, "Hypothesis for the mechanism of elevated serum copper in cancer patients", Oncology 35:22-25 (1978).
Fuchs A. G. et al., "Localization of tissue copper in mouse mammary tumors", Oncology 1989: 46:183-187.
Guerreiro J. F. et al., "Radiobiological characterization of 64CuCl2 as a simple tool for prostate cancer theranostics", Molecules 2018, 23, 2944.
Howell R W, "Radiation spectra for Auger-electron emitting radionuclides: report No. 2 of AAPM nuclear medicine task group No. 6a)", Med. Phys. 19(6) Nov./Dec. 1992 1371-1383.
International Search Report and Written Opinion received in counterpart International Application PCT/EP2023/055493 issued Jun. 14, 2023.
Jamakovic M et al., "Significance of copper level in serum and routine laboratory parameters in estimation of outspreading of Hodkin's lymphoma", Med Arh Jun. 2013; 67(3) :185-187.
Jiang L et al., "Pilot study of 64 CuCl2 for PET imaging and inflammation", Molecules 2018, 23, 502.
Kaba M et al., "Serum levels of trace elements in patients with testicular cancers" Int. Braz J Urol 2015; 41:1101-07.
Kirsi M et al., "64Cu- and 68Ga-labelled [Nle14, Lys40 (Ahx-NODAGA)NH2]-exedin-4 for pancreatic beta cell imaging in rats", Mol Imaging biol(2014) 16:255-263.
Kjaergaard K et al., "Intravenous and oral copper kinetics, biodistribution and dosimetry in healthy humans studied by [64Cu]copper PET/CT", EJNMMI Radiopharmacy and Chemistry (2020) 5-15.
Labib H A et al, "Serum copper is a simple but valuable prognostic marker in B-cell chronic lymphocytic leukemia", Int J. Hemato. Oct. 8, 2014, pp. 1-7.
Lapa C. "Exciting opportunities in nuclear medicine imaging and therapy", Journal of Clinical Medicine, 2019, 8, 1944.
Lelievre P. et al., "The multifaceted roles of copper in cancer: a trace metal element with dysregulated metabolism, but also a target or a bullet for therapy", Cancers 2020, 12 3594.
Lener M R et al., "Serum concentrations of selenium and copper in patients diagnosed with pancreatic cancer", Cancer Res Treat. 2016;48(3):1056-1064.
Lewis J S. et al., "An imaging comparison of 64-Cu-ATSM and 60-Cu-ATSM in cancer of the uterine cervix", The Journal of Nuclear Medicine, vol. 49, No. 7, Jul. 27, 2008, pp. 1177-1182.
Mali H R et al., "Changes in serum copper levels in patients with malignant diseases undergoing radiotherapy", Indian Journal of Clinical Biochemistry, 1998, 13(1), 36-40.
Manjula S. et al., "Elevetion of serum ceruloplasmin levels in brain tumours", Acta Neurol Scand 1992:86:156-158.
Marouf B H, Association between serum heavy metals level and cancer incidence in Darbandikhan and Kalar area, Kurdistan Region, Iraq, Nigerian Journal of Clinical Practice J Jun. 2018; vol. 21, issue 6 766-771.
Panichelli P. et al., "Imaging of brain tumors with copper-64 chloride: early experience and results", Cancer Biotherapy and Radiopharmaceuticals, vol. 31, numbe 6, 2016, pp. 159-167.
Peng F. et al., "PET of human prostate cancer xenografts in mice with increased uptake of 64 CuCl2", J Nucl Med 2006; 47:1649-1652.
Piccardo A. et al., "64CuCl2 PET/CT in prostate cancer relapse" Journal of Nuclear Medicine, Sep. 8, 2017, pp. 1-31.
Pinto C. I G et al, "Copper-64 chloride exhibits therapeutic potential in three-dimensional cellular models of prostate cancer", Frontiers in Molecular Biosciences, Dec. 2020, vol. 7, pp. 1-10.
Qin C et al., "Theranostics of malignant melanoma with 64CuCl2—Supplement Materials", The Journal Of Nuclear Medicine, May 2, 2014, p. 1.
Qin C. et al., "Theranostics of malignant melanoma with 64cucl2", The Journal of Nuclear Medicine, vol. 55, No. 5, May 2, 2014, pp. 812-817.
Righi S et al., "Biokinetic and dosimetric aspects of 64 CuCl2 in human prostate cancer: possible theranostic implications", EJNMMI Research, (2018) 8:18.
Saleh S A K et al., "Serum levels of selenium, zinc, copper, manganese, and iron in prostate cancer patients" Curr. Urol 2020;14;44-49.
Scanni A et al, "Variations in serum copper and ceruloplasmin levels in advanced gastrointestinal cancer treated with polychemotherapy", Tumori 65:331-338, 1979.
Stepien M et al, Circulating copper and zinc levels and risk of hepatobiliary cancers in European, British Journal of Cancer (2017) 116, 688-696.
Tiwari R. et al., "Assssment of serum copper, iron and immune complexes in potentially malignant disorders and oral cancer", Braz Oral Res. 2016;30(1) e101.
Vallabhjosula S et al., "Pharmacokinetics and biodistribution of 111 In- and 177 Lu-labeled J591 antibody specific for prostate-specific membrane antigen: prediction of 90Y-J591 radiation dosimety based on 111In or 177Lu?", The Journal of Nuclear Medicine, vol. 46, No. 4, Apr. 2005, pp. 634-641.
Zhang M et al, "Association between serum copper levels and cervical cancer risk: a meta-analysis" Bioscience Reports (2018) 38 BSR20180161.

(56) References Cited

OTHER PUBLICATIONS

Search Report and Written Opinion of PCT/EP2023/055493 issued Jun. 14, 2023.
International Preliminary Report on Patentability of PCT/EP2023/055493 issued Jun. 13, 2024.

* cited by examiner

THERAGNOSTIC METHOD FOR CANCER PATIENTS

This application is a U.S. national stage of PCT/EP2023/055493 filed on 3 Mar. 2023, which claims priority to and the benefit of U.S. Ser. No. 17/685,406 filed on 3 Mar. 2022 the contents of which are all incorporated herein by reference in their entireties.

FIELD OF THE INVENTION

The present invention relates to a radiopharmaceutical composition comprising as the active ingredient copper-64 in ionic form ($^{64}Cu^{++}$), in combination with suitable excipients and/or diluents, having a radioconcentration comprised between 50 and 3,500 MBq/mL at calibration time, optionally equal to, lower or higher than 925 MBq/mL at calibration time. Such radiopharmaceutical composition is useful in a method for treating a subject affected by a neoplasm.

BACKGROUND OF THE INVENTION

Copper, essential trace element with many physiological functions, plays an important role in tumor angiogenesis and can stimulate endothelial cell proliferation (Hu, 1998). Copper metabolism, that is tightly regulated through sophisticated homeostatic mechanism in physiological conditions, is profoundly altered in neoplastic disease together with its cellular deposition—from cytoplasm in normal tissue to intranuclear and perinuclear zones in tumors (Fuchs et al., 1989). In the past twenty years, many preclinical studies have demonstrated an effect of copper on cancer development; in particular, a copper's alteration has been observed in tumor bearing in mice and rats. Furthermore, a highly significant increase in both serum copper level and ceruloplasmin level was observed in patients with various types of tumors compared to healthy subjects (Fisher and Shifrine, 1978, Scanni et al., 1979). In particular, several authors reported an increased copper content in serum of patients affected by different tumor types such as lung cancer (Bai et al., 2019), cervical cancer (Zhang et al., 2018) and prostate cancer (Saleh et al., 2019). In addition, in glioma patients both serum copper and ceruloplasmin values showed a significantly higher concentration compared to healthy subjects or subjects affected by non-tumorous neurological diseases (Manjula et al., 1992).

Currently, the importance of copper in carcinogenesis and metastasis formation and in resistance to treatment has been explored. In addition, research work on copper deregulation in oncology and the recent understanding of copper metabolism have led to the development of numerous therapeutic strategies targeting this trace element. Despite numerous research studies and the improvement of knowledge on copper metabolism over the years, some shadow areas persist (Lelièvre et al., 2020).

The deregulated levels of copper in tumor patients can be observed thanks to the radioactive isotope Copper-64 ($^{64}Cu$). This is one of the copper isotopes that is showing its potential in the nuclear medicine field for the PET (Positron Emission Tomography) imaging, which can be or PET/CT (Computed Tomography) or PET/MRI (Magnetic Resonance Imaging). Once injected to the patient, this isotope follows the abnormal distribution of copper in the human body that can be visualized by PET. Copper-64 is the only copper isotope that possesses three decay modalities and it has a half-life (12.7 h) that allows to obtain efficient clinical imaging at delayed scan times, exploiting better target-to-background signal; furthermore, it allows for the convenient distribution of the radiopharmaceuticals after its synthesis at centralized production sites, and for easier management of scheduled activities at the clinical nuclear medicine facilities.

$^{64}Cu$ can undergo β+ emission to nickel-64, β− emission to zinc-64. Both daughter nuclides are stable. In addition to beta minus, 64Cu decays also by Auger electron emission, these electrons have an average energy of 2 keV, 126 nm range in tissue (Howell, 1992) and are considered high-LET (Linear Energy Transfer) radiation. The capability to reach the cell nuclei and to emit Auger electrons in proximity of the DNA leads to tumor cell death and this mechanism may enhance cancer therapy.

The beta plus emission gives it the capability to be a diagnostic agent, indeed different literature evidences showed the capability of 64Cu in the form of Copper Chloride ($^{64}CuCl_2$) to be a good diagnostic imaging agent in different cancer types, such as breast, prostate or melanoma, both in preclinical studies (Peng et al., 2006; Cai et al., 2014, Qin et al., 2014), but also in clinical settings. In patients affected by prostate cancer, $^{64}CuCl_2$ PET/CT seems to show superior characteristics comparing to the clinical standard $^{18}F$—FCH (Capasso et al., 2015; Piccardo et al., 2017) and also in glioblastoma patients $^{64}CuCl_2$ showed the potential to become a diagnostic agent (Panichelli et al., 2016). Instead, as mentioned above, the potential promising therapeutic use is given by the auger electron emission, but still less evidences are present in literature.

During the last few years, in the field of nuclear medicine unprecedented advances have been shown: one of the main driving forces is the so-called "theragnostic" concept that combines the use of a diagnostic biomarker with a therapeutic option. Recent developments have significantly broadened the scope of radionuclide imaging and therapies that now extends to neuroendocrine tumors, prostate cancer, or hematologic malignancies (Lapa et al., 2019).

The crucial point for the application of a theragnostic agent is the dose that, systemically administered, should reach the target tissue in sufficient quantities. Ideally, theragnostic compounds involve chemically and biologically identical compounds. Actually, the market offers the so called "theragnostic pairs" that are combinations of a diagnostic agent and a therapeutic one (Table 1). Most of them are not chemically or biologically identical, but they are similar in biodistribution and the first injection of the diagnostic agent would predict the biodistribution of the therapeutic counterpart. The diagnostic radiometals $^{111}In$ and $^{68}Ga$ and their therapeutic counterparts $^{90}Y$ and $^{177}Lu$, are all trivalent metals, which can be attached to a targeting moiety with the same chelator, but there are differences in their chemical structure, which can affect their biological properties and biodistribution (Ballinger et al., 2018).

TABLE 1

Theragnostics agents/pairs in current clinical use (Ballinger et al., 2018)

| Clinical indication | Diagnostic agent | Therapeutic agent |
|---|---|---|
| Hyperthyroidism or thyroid cancer | $^{123}I$-iodide | $^{131}I$-iodide |
| Adrenergic tumors | $^{123}I$-iobenguane | $^{131}I$-iobenguane |
| Bone metastasis from prostate cancer | $^{99m}Tc$-MDP | $^{223}Ra$ chloride |

TABLE 1-continued

| Theragnostics agents/pairs in current clinical use (Ballinger et al., 2018) | | |
|---|---|---|
| Clinical indication | Diagnostic agent | Therapeutic agent |
| Non-Hodgkins lymphoma | $^{111}$In-ibritumomab | $^{90}$Y- ibritumomab |
| Neuroendocrine tumors | $^{68}$Ga-DOTATATE | $^{68}$Lu-DOTATATE |
| Prostate cancer | $^{68}$Ga-PSMA-11 | $^{177}$Lu-PSMA-617 |

However, still the dosage regimen and its use in a theragnostic approach is still not clear to the experts in the field and can't be simply deduced due to the poor clinical data available for this treatment. In Table 2 different studies are reported, which showed the potential therapeutic use of $^{64}CuCl_2$ in different cancers such as prostate cancer, glioblastoma, melanoma, but none of them anticipates the proper theragnostic dosage regimen and approach.

Moreover, the study of Qin et al., showed the therapeutic capability of copper chloride in melanoma tumor. Specifically, as soon as the tumor diameter size reached 0.5-0.8 cm, tumor-bearing mice were administered with one dose of $^{64}CuCl_2$ (about 74 MBq) and tumor sizes were monitored over the treatment period. Results showed that the tumor growth in both the B16F10 and the A375M models under $^{64}CuCl_2$ treatment were much slower than that of the control group. The therapeutic group showed significantly improved survival, compared with that of the control group.

Taking into account this preclinical data is not possible to correlate these doses to humans. EP3071241B1 discloses a formulation and an average dose, however only generic indications are provided, moreover there are no evidences of safety and efficacy of that dose, furthermore there is no explanation of the theragnostic approach and method to use it as a theragnostic tracer.

TABLE 2

| Summary of the studies on $^{64}CuCl_2$, with particular attention to their main topic, subject of study, used radiotracer and main results | | | | | | |
|---|---|---|---|---|---|---|
| AUTHOR | TITLE | DATE | TUMOR | SUBJECT OF STUDY | RADIOTRACER | MAIN RESULTS |
| Qin et al. | Theranostics of Malignant Melanoma with $^{64}CuCl_2$ | 2014 | Melanoma | in vivo: mice bearing B16F10 or A375M tumors | $^{64}CuCl_2$ | Significantly improved survival and survival time |
| Ferrari et al. | Copper-64 Dichloride as Theranostic Agent for Glioblastoma Multiforme: A Preclinical Study | 2015 | Glioblastoma | in vivo: nude mice implanted with U-87 GM cells | $^{64}CuCl_2$ | Significant progressive decrease and, in some cases, complete regression of tumor volume. Increase in the survival rate of the treated mice |
| Catalogna et al. | The SGK1 Kinase Inhibitor SI113 Sensitizes Theranostic Effects of the 64CuCl2 in Human Glioblastoma Multiforme Cells | 2017 | Glioblastoma | in vitro: Human GBM cell lines (LI) PARI, ADF and T98G | $^{64}CuCl_2$ | $^{64}CuCl_2$ is able to induce a time and dose dependent modulation of cell viability |
| Guerreiro et al. | Radiobiological Characterization of 64CuCl2 as a Simple Tool for Prostate Cancer Theranostics | 2017 | Prostate cancer | In vitro | $^{64}CuCl_2$ | $^{64}CuCl_2$ is more cytotoxic in PCa cells than in non-tumoral cells |
| Pinto et al. | Copper-64 Chloride Exhibits Therapeutic Potential in Three-Dimensional Cellular Models of Prostate Cancer | 2020 | Prostate cancer | In vitro PCa spheroids (derived from 22RV1, DU145, and LNCaP cells | $^{64}CuCl_2$ | $^{64}CuCl_2$ is able to reduce their growth and impair the viability and reproductive ability of spheroids |

All these studies refers to a preclinical (in animals or in-vitro) application of $^{64}CuCl_2$ and none of these report clinical data. Furthermore, literature data are vague and not clear on the theragnostic approach to be used with Cu-64, its best formulation, its best radioconcentration, its dose regimen, dosing intervals that can bring to a safe and effective use.

In the study of Ferrari et al. groups of tumor implanted nude mice were treated with $^{64}CuCl_2$ to simulate single and multiple dose therapy protocols (333 MBq and 55.5 MBq/day×6 days respectively), and results were analysed to estimate therapeutic efficacy. Experiments were performed in animals bearing 3 weeks old tumors. In this study three groups of mice were compared: 30 no-treated animals, 30 animals treated with a single administration of 333 MBq of $^{64}CuCl_2$, and 30 animals treated with a multiple-dose regimen of 55.5 MBq×6 days of $^{64}CuCl_2$, one injection each day.

A theragnostic approach with $^{64}CuCl_2$ has not yet been elucidated. Despite many therapeutic advances, a number of common cancers, such as cancer of the breast, prostate, brain are still a frequent cause of death and new treatment approaches are needed. Furthermore, actually common treatments such as radiotherapy and chemotherapy are showing the development of resistance to treatment. Therefore, for cancer patients the necessity to develop new effective treatments is essential.

Furthermore, commercially available theragnostic pairs use different molecules for the diagnosis and therapy with the risk to do not have the exact biodistribution of the tracer, for the prediction of the therapeutic one, furthermore with the lack of monitoring the response to treatment with the same therapeutic dose.

In view of the drawbacks of the prior art, it would be highly advantageous to provide an efficacious theragnostic approach for the administration of $^{64}CuCl_2$ to patients affected by tumors in both adults and pediatric population.

The issue of a safe and effective delivery of therapeutic doses of $^{64}CuCl_2$ is solved by the present invention.

DESCRIPTION OF THE INVENTION

The present invention is based on the discovery that, differently from what has been reported until now, Copper-64 in the form of salt (e.g. $^{64}CuCl_2$) can be used as a real theragnostic agent, not only as a component of a theragnostic pair. In other words, the same chemical entity (copper) and the same isotope (64) can be used both for patient selection and for therapeutic use. The exactly same product gives the dual action and the first injection can predict exactly the biodistribution of the following injections. The first step consists of using the composition to evaluate the eligibility of a subject affected by a neoplasm for a specific therapy or treatment and it is also herein referred to as the "selection step", meaning that this step allows to select a subject that can undergo a following specific therapy or treatment. If the subject results to be eligible for the treatment and is selected for the treatment, then the subject is treated by administering a therapeutically efficient amount of a radiopharmaceutical composition comprising as the active ingredient copper-64 in ionic form ($^{64}Cu^{++}$), in combination with suitable excipients and/or diluents, having a radioconcentration comprised between 50 and 3,500 MBq/mL at calibration time. In particular, the present invention relates to a radiopharmaceutical composition comprising as the active ingredient copper-64 in ionic form ($^{64}Cu^{++}$), in combination with suitable excipients, and/or diluents, having a radioconcentration comprised between 50 and 3,500 MBq/mL at calibration time, optionally equal to, lower or higher than 925 MBq/mL at calibration time.

Another object of the present invention is the radiopharmaceutical composition comprising as the active ingredient copper-64 in ionic form ($^{64}Cu^{++}$), in combination with suitable excipients, and/or diluents, having a radioconcentration comprised between 50 and 3,500 MBq/mL at calibration time, optionally equal to, lower or higher than 925 MBq/mL at calibration time for use as a medicament.

A further object of the present invention is a method of treatment of a neoplasm comprising the administration of a radiopharmaceutical composition comprising as the active ingredient copper-64 in ionic form ($^{64}Cu^{++}$), in combination with suitable excipients and/or diluents in a saline solution, having a radioconcentration comprised between 50 and 3,500 MBq/mL at calibration time, optionally equal to, lower or higher than 925 MBq/mL at calibration time.

Still another object of the present invention is a radiopharmaceutical composition comprising as the active ingredient copper-64 in ionic form ($^{64}Cu^{++}$) having a radioconcentration comprised between 50 and 3,500 MBq/mL at calibration time, optionally equal to, lower or higher than 925 MBq/mL at calibration time, for use in the preparation of a medicament.

To evaluate the preferred composition to be used in a clinical trial with a theragnostic approach, different in vitro tests have been conducted both from a pharmaceutical and biological point of view.

The inventor showed the capability of $^{64}CuCl_2$ to cause a cell-killing effect on tumor cell in different tumor lines. The capability resulted improved at a radioconcentration higher than 925 MBq/mL compared to lower concentrations. This is the first time that the impact of the drug radioconcentration has been correlated to the cell-killing effect for the translation to humans. The inventor performed internalization and survival studies on different cancer cell lines (U87MG [glioblastoma], PC-3[prostate cancer], CAMA1 [breast cancer], C8161[melanoma], HT-29[colorectal cancer]), A549 [lung cancer] applying the same amount (dose) of radioactivity (eg. 10 MBq), but at different radioconcentrations, e.g. 2,775 MBq/mL vs. 1,850 MBq/mL, vs. 925MBq/mL.

The results showed that in all the cell lines there was a direct impact of radioconcentration on cell uptake 4 h after treatment: significantly greater with the higher concentrations compared to the lowest concentration (FIG. 1). The increased uptake with the concentration of 2,775 MBq/mL has brought also to an increased cell-killing effect at 24 h after treatment as shown, as an example, in the cell survival curve of U87MG line (FIG. 2). This effect of the radioconcentration could have a great impact on patients for the optimization of treatment. In fact, in consideration of the mechanism through which $^{64}Cu$ reaches the tumor cell, the different radioconcentrations, that is to say "the number of nuclear disintegrations per unit time in a given amount of the preparation", can influence the biodistribution *in vivo*. Without wishing to be bonded by any theory, indeed, the higher number of nuclear disintegrations of the isotope can reduce the link stability of the cation with the circulating proteins responsible to transport copper to the target organs. The lower stability linkage with carrier proteins brings to a greater availability of the isotope for the tumor cell and this is connected to a higher genotoxic effect.

In general, for radiopharmaceuticals the radioactive concentration influences the radiochemical purity and the decrease in radioactive concentration increase the radiochemical purity. Therefore, it would not be obvious for a skilled person that increasing the radioconcentration of $^{64}Cu$ radiopharmaceuticals can bring to a benefit for the biological effect: theoretically the increasing of radioconcentration generally brings to a higher content of impurities including "non-radioactive" copper. However, contrary to what one may expect, in this invention formulations with the higher radioconcentrations are characterized by a high level of purity: a low content of the "non-radioactive" copper and a high content of "radioactive" copper-64 ions, that are able to release an higher content of Auger electron in the tumor cell. In comparison to the other formulation (925 MBq/mL) this gives an improved therapeutic effect.

In consideration of our *in-vitro* tests, $^{64}CuCl_2$ 2,775 MBq/mL at calibration time was chosen as the preferred radioconcentration to be injected to patients, as the most suitable for a theragnostic approach, showing advantages from both an efficacy point of view and taking into account a practical aspect. Indeed, this high radioconcentration solves the problem to have a big amount of radioactivity necessary for the treatment in a reduced volume, considering that low radioconcentration values corresponds to high volumes, whereas high radioconcentration values are associated to smaller values. The reduction of the volume represents an advantage from a radioprotection side, in fact let the nurse to inject directly to the patient, reducing the time of exposure compared to administering per continuous infusion, and increasing the patient's compliance.

However, further clinical evidences (also reported in the Examples' section) have shown that even lower radioconcentrations (equal to or lower than 925 MBq/mL) are effective in the treatment of a neoplasm, if the administration route is intravenous by infusion and the volume of the radiopharmaceutical composition to be administered is regulated, on the basis of the dose to be administered to the subject.

PET/CT imaging evaluations obtained with lower or higher concentrations of $^{64}CuCl_2$, showed the uptake in the neoplastic cell, this let the inventor to understand that, the $^{64}CuCl_2$ is able to enter neoplastic cell, and consequently it can induce a therapeutic effect, independently of the route of administration.

Considering that in the subject affected by a neoplasm there is a different homeostasis of copper and a deregulation of copper transporters, $^{64}Cu$ follows this abnormal metabolic pathway, reaching the neoplastic lesion, independently from the route through which $^{64}Cu$ is introduced in the human body.

The radiopharmaceutical composition of the invention may be administered to the subject by any routes of administration, including enteral, parenteral, inhalation, oral and transcutaneous. Preferably the route of administration is parenteral, including intravenous, intramuscular, intradermal, subcutaneous, intratumoral, intracavity and intrathecal. More preferably, the route of administration is intravenous by injection, by infusion or by an implant.

According to a specific embodiment of the invention, the administration route of the radiopharmaceutical composition of the invention is by injection.

According to another specific embodiment of the invention, the administration route of the radiopharmaceutical composition of the invention is by infusion.

According to a further specific embodiment of the invention, the administration route of the radiopharmaceutical composition of the invention is intratumoral.

According to another specific embodiment of the invention, the administration route of the radiopharmaceutical composition of the invention is intracavity.

According to a further specific embodiment of the invention, the administration route of the radiopharmaceutical composition of the invention is intrathecal.

The radiopharmaceutical composition of the invention may be administered to the subject also with any medical device.

According to specific embodiments of the invention, the radioconcentration of the radiopharmaceutical composition of the invention is comprised between 930 MBq/mL and 3,500 MBq/mL at calibration time, preferably when the administration route is intravenous by injection. According to specific embodiments of the invention, the radioconcentration of the radiopharmaceutical composition of the invention is comprised between 1,000 MBq/mL and 2,800 MBq/mL at calibration time, preferably when the administration route is intravenous by injection. According to specific embodiments of the invention, the radioconcentration of the radiopharmaceutical composition of the invention is 1,850 MBq/mL preferably when the administration route is intravenous by injection.

According to specific embodiments of the invention, the radioconcentration of the radiopharmaceutical composition of the invention is 2,775 MBq/mL at calibration time, preferably when the administration route is intravenous by injection.

According to an embodiment, the pharmaceutical composition is a solution for injection that can be diluted with NaCl 0.9% before injection.

According to other specific embodiments of the invention, preferably when the administration route is intravenous by infusion, the radioconcentration of the radiopharmaceutical composition of the invention is comprised between 50 MBq/mL and 925 MBq/mL at calibration time.

According to other specific embodiments of the invention, preferably when the administration route is intravenous by infusion, the radioconcentration of the radiopharmaceutical composition of the invention is comprised between 80 MBq/mL and 750 MBq/mL at calibration time.

According to further specific embodiments of the invention, preferably when the administration route is intravenous by infusion, the radioconcentration of the radiopharmaceutical composition of the invention is comprised between 100 MBq/mL and 600 MBq/mL at calibration time.

According to further specific embodiments of the invention, preferably when the administration route is intravenous by infusion, the radioconcentration of the radiopharmaceutical composition of the invention is comprised between 200 MBq/mL and 450 MBq/mL at calibration time, optionally it is 277 MBq/mL at calibration time, optionally it is 350 MBq/mL at calibration time.

According to a further specific embodiment of the invention, preferably when the administration route is intravenous by infusion, the radioconcentration of the radiopharmaceutical composition of the invention is equal to 925 MBq/mL at calibration time.

According to a further specific embodiment of the invention, preferably when the administration route is intravenous by injection, the radioconcentration of the radiopharmaceutical composition of the invention is equal to 1,850 MBq/mL at calibration time.

According to a further specific embodiment of the invention, preferably when the administration route is intravenous by injection, the radioconcentration of the radiopharmaceutical composition of the invention is equal to 2,775 MBq/mL at calibration time.

Counter-ions may be present in the radiopharmaceutical composition of the invention, such as for example chloride, acetate, citrate ions etc., to prepare a solution at a pH suitable for injection.

For example, the formulation can be composed by 5% of $^{64}CuCl_2$, 2% acetate buffer solution, 10-93% 0,9% NaCl solution or for example the formulation can be composed by 8% of $^{64}Cu(OAc)_2$, 4% of acetate buffer solution, 12-88% of water for injection (WFI), 1% antioxidant (e.g. ascorbic acid).

According to another embodiment of the invention, the specific activity of this radiopharmaceutical composition is comprised between 5.102 and 5.104 MBq of $^{64}Cu$/micrograms of copper.

According to another embodiment of the invention, the specific activity of this radiopharmaceutical composition is comprised between 1,000 and 10,000 MBq of $^{64}Cu$/micrograms of copper, optionally it is 5,000 MBq of $^{64}Cu$/micrograms of copper.

The radiopharmaceutical composition is preferably a sterile solution that can be used as a ready-to-use solution for intravenous use.

The radiopharmaceutical composition preferably has a pH suitable for direct injection and comprised between 4-8.

Another embodiment of the present invention relates to the radiopharmaceutical composition of the invention, as previously described, for use in the treatment of neoplasms.

According to an embodiment of the invention, a treatment of a neoplasm may have a theragnostic approach, thus comprising a first step to evaluate the eligibility of a subject for the treatment, a further step to treat the selected subject and, optionally, a further step to monitor the response of the subject to the treatment.

In other words, such theragnostic approach is a method for treating a neoplasm in a human subject, which comprises the following steps:

a) administering an effective amount of a radiopharmaceutical composition comprising as the active ingredient copper-64 in ionic form ($^{64}Cu^{++}$), in combination with suitable excipients, and/or diluents to evaluate the eligibility of said subject for a subsequent treatment;

b) acquiring an image by PET/MRI or PET/CT of said subject, to evidence any copper-64 uptake by neoplastic cells of the cancer lesions;

c) in case of evidence of copper-64 uptake by neoplastic cells, subjecting the subject to a treatment cycle by administering for therapeutic purpose to said subject a therapeutically effective amount of a radiopharmaceutical composition comprising as active ingredient copper-64 in ionic form ($^{64}Cu^{++}$), in combination with suitable excipients, and/or diluents.

The purpose of steps (a) and (b) in the above method is to select a subject for the treatment by evaluating $^{64}CuCl_2$ uptake in the lesions, as determined by PET/CT or PET/MRI imaging in said subject. In case the imaging evaluation shows copper-64 uptake, the subject can be included in the treatment, otherwise, in case there is no uptake, the treatment is not advisable. In case there is copper uptake from the tumor lesion, this can also have a predictive value of response to treatment.

According to step a), the patient firstly receives one administration of $^{64}CuCl_2$, a single dose between 3 MBq/kg and 14 MBq/kg, preferably between 5.3 MBq/kg and 13 MBq/kg. As an example, a patient of 70 kg can receive a dose of 371 MBq of $^{64}CuCl_2$, typically by intravenous injection. For a child of 25 kg the diagnostic dose is 132.5 MBq, preferably the dose should be in the range 130-200 MBq.

According to step b) to acquire images of patient's body a PET/CT or PET/MRI imaging is performed, preferably from 1 h to 4 h after $^{64}CuCl_2$ injection and the PET imaging is evaluated to evidence the uptake of $^{64}CuCl_2$ in the cancer lesion of the patient. The PET imaging analysis after the dose would consider a lesion as positive determining the target to background ratio (TBR).

According to a specific embodiment of the invention, the TBR value of a lesion of a human subject affected by a neoplasm is measured to evidence the uptake of Copper-64 in the lesion of the subject. TBR is a value that is obtained by an objective evaluation performed by method that includes an output from a computer that does not require the interpretation from a medical doctor. In particular, TBR is the ratio between the maximum SUV ($SUV_{max}$) of each region of interest and the maximum SUV (Standardized Uptake Value) of the level of some normal tissues to be considered "background tissue" (BKG). The measurement of the $SUV_{max}$ of each collection site corresponding to the lesion must be carried out by positioning a VOI (Volume Of Interest), which fully includes the collection site.

TBR will be calculated as follow:

For lymph node lesions: $SUV_{max}$ (Lesion)/$SUV_{max}$ (mediastinal)

For bone lesions: $SUV_{max}$ (Lesion)/$SUV_{max}$ (muscle)

For visceral lesions: $SUV_{max}$ (Lesion)/$SUV_{max}$ (contralateral organ or mediastinal)

The arithmetic average of the $SUV_{max}$ values measured on the VOI drawn on the gluteal muscles of each side will be calculated and it will be referred to as the muscle background uptake value. For the other tissues, the maximum SUV value measured for the single VOI selected will be used. A lesion is determined as positive for $^{64}CuCl_2$ uptake (i.e. evidencing an uptake of $^{64}CuCl_2$), if TBR results equal to or higher than 5. A lesion is determined as negative for $^{64}CuCl_2$ uptake if the TBR is lower than 5.

According to an embodiment the invention, the TBR is used as the objective parameter for patient selection.

If patient has at least one lesion for which TBR is equal to or higher than 5, the patient can be selected for treatment. If patient has no lesions for which TBR is equal to or higher than 5, the patient cannot be selected for treatment.

Moreover, the TBR analyzed in the PET/CT or PET/MRI after the first administration of the composition, is also used as an objective parameter to predict treatment response.

The results reported in the Examples section show that the TBR of the non-responder patient was higher compared to the responder ones. In particular, on the basis of the clinical data, TBR value >25 resulted in non-responder patients and TBR comprised between 5 and 25 resulted in patients classified as responders.

Therefore TBR, in addition to represent an index of tumor uptake in patients, can be a predictive index of $^{64}CuCl_2$ treatment response. The PET/CT or PET/MRI results very useful to select the proper patient that can undergo $^{64}CuCl_2$ treatment, thus avoiding to expose the patient to the risk to undergo an unsuccessful treatment.

The evaluation can be an empirical evaluation of copper-64 uptake. The PET/CT or PET/MRI output can show an output which does not require the interpretation of a medical doctor. Thus, in one embodiment of the invention, the method comprises the step of evaluating copper-64 uptake as a computer output which is at a certain predetermined threshold. Copper-64 uptake and TBR evaluated this way can be used as eligibility criteria for treatment.

The objective of this method is to select the patient, which can be a good responder patient to the $^{64}CuCl_2$ treatment.

A "good responder" patient is a patient selected among a population, which shows a better response to the treatment in comparison to the patient that has not been selected with the above mentioned method (random selection) and/or a patient which shows lower side effects/adverse events to the treatment in comparison to the patient that has not been selected with the above mentioned method (random selection).

This selection is allowed thanks to the PET/CT and/or PET/MRI, indeed a different imaging modality (i.e. MRI, CT, bone scan or PET/CT with other radioactive compounds different from the radioisotope 64Cu) cannot select the patient for treatment considering that cannot show if the drug can be internalize by the tumor cells of that specific patient, and consequently cannot predict if that patient can benefit from the treatment. The selection step is necessary to avoid the risk for patient to start an unsuccessful and toxic treatment.

If the patient results to be eligible for the treatment and is selected for the treatment, the method then further comprises a step of treating cancer in said patient selected for a treatment by administering a therapeutically efficient amount of $^{64}CuCl_2$. The treatment can start the same day of the administration for selection or from 1 day to 4 weeks after the administration for selection.

The present inventors have shown that copper-64 in certain concentrations and amounts can be used in a method for treating neoplasms which can internalize copper-64. The neoplasms are therefore specific neoplasms that a more sensitive to copper-64 treatment. Thus, one embodiment of the present invention relates to the use of copper-64 for the treatment of a neoplasm which can internalize copper-64. A further embodiment of the present invention relates to the use of copper-64 for the preparation of a medicament for the treatment of a neoplasm which can internalize copper-64.

According to a specific embodiment of the invention, step a) previously mentioned may optionally be preceded by the following steps:

i) collecting a blood sample from the human subject;

ii) detecting the content of chemical copper in such sample;

wherein step (c) is effected only if serum copper level detected in the sample is over normal ranges.

The purpose of step (ii) is to measure the content of copper in the blood, as it may act as a biomarker of tumor activity. In particular, increased levels of circulating copper over normal ranges indicate increased use of copper by tumor cells. Maximum serum copper levels in blood may vary depending on the analytical method used to measure them. Serum copper level over normal ranges is over 60 μg/dL, optionally over 150 μg/dL.

According to an embodiment of the invention, if the serum copper level in the blood sample of a human subject affected by a neoplasm, is higher than 60 μg/dL, preferably higher than 150 μg/dL, then the subject is treated by administering a therapeutically efficient amount of a radiopharmaceutical composition comprising as the active ingredient copper-64 in ionic form ($^{64}Cu^{++}$), in combination with suitable excipients and/or diluents, having a radioconcentration comprised between 50 and 3,500 MBq/mL at calibration time. Thus, the present inventors have shown that high levels of copper in the blood can be used as a positive indicator for the outcome of copper-64 treatments. The neoplasms are therefore specific neoplasms that a more sensitive to copper-64 treatment if the subject has elevated blood copper levels. An embodiment of the present invention relates to a method for treating neoplasms in individuals with elevated blood copper levels, as described above. Thus, one embodiment of the present invention relates to the use of copper-64 for the treatment of a neoplasm of an individual with elevated blood copper levels. A further embodiment of the present invention relates to the use of copper-64 for the preparation of a medicament for the treatment of a neoplasm of an individual with elevated blood copper levels. According to an embodiment of the invention, the dose that can be injected for therapeutic scope to have a safe and effective action is from a minimum of 7 MBq/kg to a maximum of 210 MBq/kg.

According to a specific embodiment of the invention, the dose that can be injected for therapeutic scope to have a safe and effective action is from a minimum of 13 MBq/kg to a maximum of 105 MBq/kg.

The dose will be calculated on the basis of the weight of the subject. For example, a patient of 70 kg can receive a dose between 1,850 MBq and 4,810 MBq. For a child of 25 kg the dose can be between 325 MBq to 2,625 MBq. In specific embodiments, a therapeutically efficient amount of the composition is administered to said subject 1 to 7 times per treatment cycle. The cycle can be repeated more than one time, preferably from one cycle to seven. The frequency of administration can comprise from 1 to 3 administrations per week. For each treatment cycle, the dosage regimen can comprise the administration of an increasing dose or of a fixed dose to the patient. At least 15 days should normally pass between each cycle and the next.

If an increasing dose regimen is used, typically the first dose is an initial therapeutic dose ($X_1$) and the following doses may be calculated as follow:

| | |
|---|---|
| 1st dose | $X_1$ MBq |
| 2nd dose | $X_2 = (X_1 + 33\% \text{ of } X_1)$ MBq |
| 3rd dose | $X_3 = (X_2 + 25\% \text{ of } X_1)$ MBq |
| 4th dose | $X_4 = (X_3 + 20\% \text{ of } X_1)$ MBq |
| 5th dose | $X_5 = (X_4 + 17\% \text{ of } X_1)$ MBq |
| 6th dose | $X_6 = (X_5 + 14\% \text{ of } X_1)$ MBq |
| 7th dose | $X_7 = (X_6 + 11\% \text{ of } X_1)$ MBq |

An exemplary treatment regimen comprises the following administrations for each cycle to an adult patient: 1$^{st}$ dose=1, 850 MBq, 2$^{nd}$ dose=2,460MBq, 3$^{rd}$ dose=2,922 MBq, 4$^{th}$ dose=3,292 MBq, 5$^{th}$ dose=3,606 MBq, 6$^{th}$ dose=3,865 MBq, 7$^{th}$ dose=4,068 MBq, where the total activity administered is equal to 22,063 MBq per cycle.

A different exemplary treatment regimen comprises the following administrations for each cycle to an adult patient: 1$^{st}$ dose=4,810 MBq, 2$^{nd}$ dose=4,810 MBq, 3$^{rd}$ dose=4,810 MBq, 4$^{th}$ dose=4,810 MBq, 5$^{th}$ dose=4,810 MBq, 6$^{th}$ dose=4,810MBq, 7$^{th}$ dose=4,810 MBq, where the total activity administered is equal to 33,670 MBq per cycle.

In certain aspects the administration of $^{64}CuCl_2$ to a subject that has been selected for that treatment can have an incidence on the volume of the tumor lesion that can remain stable in comparison to the volume of the lesions before treatment (no progression, no new lesions identified, stable disease).

In certain aspects the administration of $^{64}CuCl_2$ to a subject that has been selected for that treatment can have an incidence on the volume of the tumor lesion that results reduced at 50% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 60% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 70% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 80% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 90% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 95% in comparison to the volume of the lesions before treatment (reduction of lesions, no new lesions, partial response).

In certain aspects the administration of $^{64}CuCl_2$ to a subject that has been selected for that treatment can have an incidence on the volume of the tumor lesion that results reduced at 100% in comparison to the volume of the lesions before treatment (disappearance of lesions, no new lesions, complete response).

In certain embodiments the administration of $^{64}CuCl_2$ to a subject that has been selected for that treatment can inhibit, and/or delay, and/or reduce tumor growth in that subject. In certain aspects the growth of the tumor is delayed by at least 10%, 20%, 30%, 40% 50%, 60%, 70%, 80%, 90% to the predicted growth of the tumor without the treatment.

In certain embodiments, the administration of the drug to a subject that has been selected for that treatment can increase the length of survival of the subject in comparison to the predicted length of survival of the subject without the treatment. In certain aspects the length of survival is increased by at least 30 days, 60 days, 90 days, 180 days, 365 days, 547 days, 730 days in comparison to the predicted length of survival of the subject without the treatment.

According to one embodiment, the cycle can be repeated more than one time, before selecting patient for a further cycle of treatment, a PET/CT or PET/MRI with $^{64}CuCl_2$, and/or a conventional imaging for example MRI, CT, SPECT, US, PET with other radioisotopes differently from Cu-64 is performed at least after 15 days, preferably after 30 days, after the end of the last treatment. If the PET/CT or PET/MRI and/or a conventional imaging for example MRI, CT, SPECT, US, PET with other radioisotopes differently from Cu-64 evaluation show response to treatment, as defined above, the patient can proceed with a further cycle of treatment. The treatment and the dose calculation can be applied both to an adult patient and to pediatric population.

These doses and dosage schemes have never been tested before for efficacy and safety and do not derive from the preclinical literature data. In fact, starting from all preclinical data, it is possible to extrapolate and estimate the injectable dose to the patient, the extrapolation takes into account the differences in organ weights between man and animal, assuming a similar kinetic trend. The inventors performed a simulation with OLINDA software taking into account the possible variation of the organs exposed to greater risks, which is kidney in mouse while liver in humans (Linder et al., 1998). However, the extrapolation cannot be translated to humans, because the converted dose for humans resulted very high. Therefore, the doses were defined starting from the diagnostic dose.

Furthermore, this is the first time, in which an evaluation of the safety profile and the Dose Limiting Toxicity was performed. No treatment related toxicities were registered associated to liver/kidney and red marrow distribution.

The disclosure also relates to a pharmaceutical composition as described in the previous section for use as PET/CT or PET/MRI imaging agent in monitoring and determining whether a subject responds or not to $^{64}CuCl_2$ treatment.

After each therapeutic injection it is possible to perform a PET/CT or PET/MRI to the subject to monitor response to the treatment without the necessity to inject other tracers. The monitoring of response to treatment let to control the trend of the disease and the response of the body to the treatment, including monitoring possible toxicities evaluating the biodistribution. Therefore, for example after the $4^{th}$ therapeutic dose of the first cycle of therapy the physician decide to perform a PET/CT scan to evaluate if continuing the treatment or interrupting, preventing the continuation of the treatment in patient that does not answer to the treatment.

The results of the PET/CT or PET/MRI imaging can be compared with a standard imaging for example MRI, CT, SPECT, US, PET with other radioisotopes differently from Cu-64. Nowadays there are no PET techniques evaluated to monitor response to $^{64}CuCl_2$ treatment.

The human subject that undergo the treatment can be male or female, can be an adult patient or a child.

According to an embodiment of the invention, the neoplasm that can be treated with the radiopharmaceutical composition of the invention may be an *in situ* neoplasm, a malignant neoplasm and a neoplasm of uncertain or unknown behavior. Malignant neoplasms are also simply known as “cancers” or “carcinomas”. The invention can be used for all the cancer or tumor types that are able to have an uptake of copper, in consideration of the same mechanism used for $^{64}Cu$ internalization by the tumour cell. Examples of cancers that can be treated with the radiopharmaceutical composition of the invention are pancreatic, prostate, brain, in particular, glioblastoma and astrocytoma, breast, ovary, urogenital, head-neck, esophagus, stomach, intestines, colon and lung cancer, as well as melanoma, leukemia and lymphoma.

An object of the present invention is the radiopharmaceutical composition as mentioned above, for use as a medicament in the treatment of head-neck or brain cancer, in particular glioma, glioblastoma or astrocytoma.

Another object of the present invention is the radiopharmaceutical composition as mentioned above, for use as a medicament in the treatment of prostate cancer or metastatic prostate cancer.

A further object of the present invention is the radiopharmaceutical composition as mentioned above, for use as a medicament in the treatment of breast or ovary cancer.

Another object of the present invention is the radiopharmaceutical composition as mentioned above, for use as a medicament in the treatment of esophagus, stomach, intestines or colon cancer.

Another object of the present invention is the radiopharmaceutical composition as mentioned above, for use as a medicament in the treatment of lung cancer.

Another object of the present invention is the radiopharmaceutical composition as mentioned above, for use as a medicament in the treatment of leukemia or lymphoma.

Another object of the present invention is the radiopharmaceutical composition as mentioned above, for use as a medicament in the treatment of a neuroendocrine tumor.

Another object of the present invention is the radiopharmaceutical composition as mentioned above, for use as a medicament in the treatment melanoma.

A specific object of the invention is the radiopharmaceutical composition comprising as the active ingredient copper-64 in ionic form ($^{64}Cu^{++}$), in combination with suitable excipients and/or diluents in a saline solution having a radioconcentration at calibration time of 2,775 MBq/mL for use as a medicament in the treatment of glioblastoma, wherein the composition is to be administered by injection.

A specific object of the invention is the radiopharmaceutical composition comprising as the active ingredient copper-64 in ionic form ($^{64}Cu^{++}$), in combination with suitable excipients and/or diluents in a saline solution having a radioconcentration at calibration time of 2,775 MBq/mL for use as a medicament in the treatment of prostate cancer or metastatic prostate cancer, wherein the composition is to be administered by injection.

The possibility to use the composition in different tumor types is linked to the mechanism of copper internalization in the tumor cell, that is the same independently from the tumor type. Indeed, in the tumor there is an higher content of copper in comparison to normal cells and $^{64}Cu^{2+}$ follows this abnormal copper homeostasis replacing chemical $Cu^{2+}$ ions. In the blood stream, $^{64}Cu^{2+}$ ions can be bound to plasma proteins (such as ceruloplasmine, albumin and transcuprein) and these proteins transfer $^{64}Cu^{2+}$ ions to the outer cell membrane, where they are reduced to $^{64}Cu^{+}$ ions by reductase enzymes. In this reduced oxidation state, Cutions are then transported across the cell membrane by the human copper transporter 1 (CTR1) and once into the cell copper trafficking is mediated by chaperones, which typically receive $Cu^{+}$ immediately after it enters the cell. These chaperones deliver $Cu^{+}$ ions to cytosolic SOD1, cytochrome C oxidase (COX) in the mitochondria, ATP7A and ATP7B are responsible to transport copper to the trans-Golgi network, and the antioxidant protein (ATOX1) into the nucleus (Boschi et al., 2018).

The proof of the $^{64}CuCl_2$ internalization in tumor cells is evident from the preclinical studies with microPET, but also from clinical studies. Jorgensen and collaborators studied with microPET, after administration of $^{64}CuCl_2$, mice transplanted with a series of 5 human neoplastic cell lines, including ovarian cancer, head and neck, neuroendocrine lung carcinoma, colorectal cancer, glioblastoma showing a significant uptake of $^{64}Cu^{2+}$ by neoplastic tissues (Jorgensen et al., 2013). This capability of $^{64}CuCl_2$ to be a tracer of copper homeostasis has been also confirmed in the clinical setting for example in prostate cancer (Piccardo et al., 2017), glioblastoma (Panichelli et al., 2016) urological malignancies (Mascia et al., 2021) and non-small cell lung cancer (García-Pérez et al., 2020) showing that the radioisotope has the capability to enter the tumor cell of a very different kind of tumors.

Several studies correlate $^{64}CuCl_2$ uptake by the tumor cells to the overexpression of CTR1 in tumors, showing its potential as a promising target for molecular imaging, and its role in making $^{64}CuCl_2$ selective for tumor cells.

In the study of Kim et al. in human breast cancer cells, an increased uptake of $^{64}CuCl_2$ resulted correlated to a CTR1 overexpression (Kim et al., 2014), while, as confirmation, inhibition of CTR1 in prostate cancer resulted in a decreased uptake of $^{64}CuCl_2$ (Cai et al., 2014). The involvement of CTR1 in $^{64}CuCl_2$ uptake have been demonstrated also in other tumor types such as hepatocellular carcinoma (Peng et al., 2005), prostate cancer (Peng et al., 2006; Cai et al., 2014), melanoma (Qin et al, 2014), neuroblastoma (Pamar et al., 2018), Lung (Wang et al., 2020), ovarian cancer, head and neck, colorectal cancer and glioblastoma (Jorgensen et al., 2013).

Other transporters/chaperones influence $^{64}Cu$ uptake, such as ATOX1, that results overexpressed in different tumor types such as colorectal cancer, breast cancer, lung cancer, melanoma and involved in copper transport (Cai H et al, 2013; Beaino et al., 2014; Karginova et al., 2019; Kim et al., 2019).

Considering that CTR1 and ATOX1 are correlated to $^{64}CuCl_2$ uptake, they have the potential to become predictive biomarkers of treatment response and useful biomarkers for patient selection.

Finally, the tumors that internalize $^{64}CuCl_2$, and for which the tracer is successfully visualized by PET/CT or PET/MRI, can be treated with $^{64}CuCl_2$, highlighting the high potential of using $^{64}CuCl_2$ as a theragnostic agent.

The radiopharmaceutical composition and the method of the invention can bring a great contribution to patient care comparing to existing therapies. In particular, with respect to other treatments with radiopharmaceuticals defined as theragnostic, which contemplate the injection of two different doses and two different compounds, the method according to the invention envisions that the same radiopharmaceutical can be used as select the subject to be treated, to treat the subject selected and to monitor the response of the subject to the treatment; this brings the following advantages to patients:

- Reduce the adverse effect that can arise from multiple drug interactions: Patients avoid the injection of different compounds therefore this approach can reduce the adverse effect that can arise from multiple drug interactions without the necessity to administer another PET/CT imaging agent for diagnosis or for monitoring response to treatment, it is reduced the risk of adverse events occurrence associated to drug-drug interactions
- Monitoring response to treatment in real-time: during treatment is not necessary to inject a further dose of another radiopharmaceutical to monitor response to treatment: this treatment approach has the great advantage that with a PET/CT scan the drug effects can be monitored in real-time during the therapy course whenever clinician retain proper. This is essential in view of a personalized medicine, in fact the control of the response to therapy would let the physician to decide if interrupting the treatment if retained not effective for the patient or continue without losing time for waiting for the administration of another therapeutic agent. For example, after the injection of the $4^{th}$ therapeutic dose of $^{64}CuCl_2$ a PET/CT is performed without the necessity of administering another and different drug for the assessment of tumor response.
- Predict the proper therapy choice: with the first diagnostic injection the physician can verify if the patient is appropriate to start the treatment or not. In case with the first injection there is no uptake, the patient can be redirect towards another treatment, on the other hand, in case there is significant uptake, it can be expected to have good possibility for treatment to be effective. Therefore, this can be a fast approach to predict if the treatment can be used or not for that particular subject
- Increase the compliance of patient: the patients shows more compliance if the same drug can be used for multiple scopes because he feels more confident on a drug that has already been injected without giving side effect, furthermore the patient appreciate the reduction of the number of drugs that receive.
- Reduced exposure of the hospital personnel: the use of the same tracer for diagnostic, therapeutic and monitoring response to treatment, reduce the exposure of the personnel during the manipulation steps of the product (e.g. reduce exposure in preparing different doses)

Definitions

"Theragnostics" (or "theragnostic/theranostic" method) is here intended to be a treatment strategy that combines therapeutics with diagnostics. It associates both a diagnostic test that identifies patients most likely to be helped or harmed by a new medication, and targeted drug therapy based on the test results.

A "neoplasm" is here intended to be a type of abnormal and excessive growth of tissue. This abnormal growth usually forms a mass, when it may be called "tumor". The process that occurs to form or produce a neoplasm is called "neoplasia". According to ICD-10 (Neoplasms—International Statistical Classification of Diseases and Related Health Problems 10th Revision (ICD-10) Version for 2010. World Health Organization. Retrieved 19 June 2014) neoplasms are classified into four main groups: benign neoplasms, in situ neoplasms, malignant neoplasms, and neoplasms of uncertain or unknown behavior. Malignant neoplasms are also simply known as "cancers" or "carcinomas".

According to the present invention, the expressions "treatment" or "treating" are intended to refer to activities designed to cure, ameliorate, inhibit or mitigate the symptoms or delay the progression of a disease or a pathological condition.

The expression "radiopharmaceutical" composition is intended here to refer to a pharmaceutical composition comprising a radioactive isotope.

According to the present invention, the expression "radioconcentration" is intended to mean concentration of a radioisotope. It is measured in mCi/mL or MBq/mL at the time of calibration (TOC), generally at the end of synthesis (EOS).

With the term "excipient", it is intended here to refer to conventional excipients, i.e. inert compounds towards the active ingredient of a composition.

The invention will now be described by making reference to the following non-limiting Examples.

Survival curve of U87MG treated with the same dosage range but at three different concentrations C1=925 MBq/mL, C2=1,850 MBq/mL, C3=2,775 MBq/mL. Value are expressed as mean±SEM. (p≤0.01 *p≤0.001 compared to cell treated with C1). D0=No treatment, D1=0.0034 MBq, D2=0.034 D3=0.34, D4=1.7 MBq, D5=3.4MBq. C3 let to have at D4 and D5 an improved cell killing-effect of about 30% compared to C1.

Figure 1:
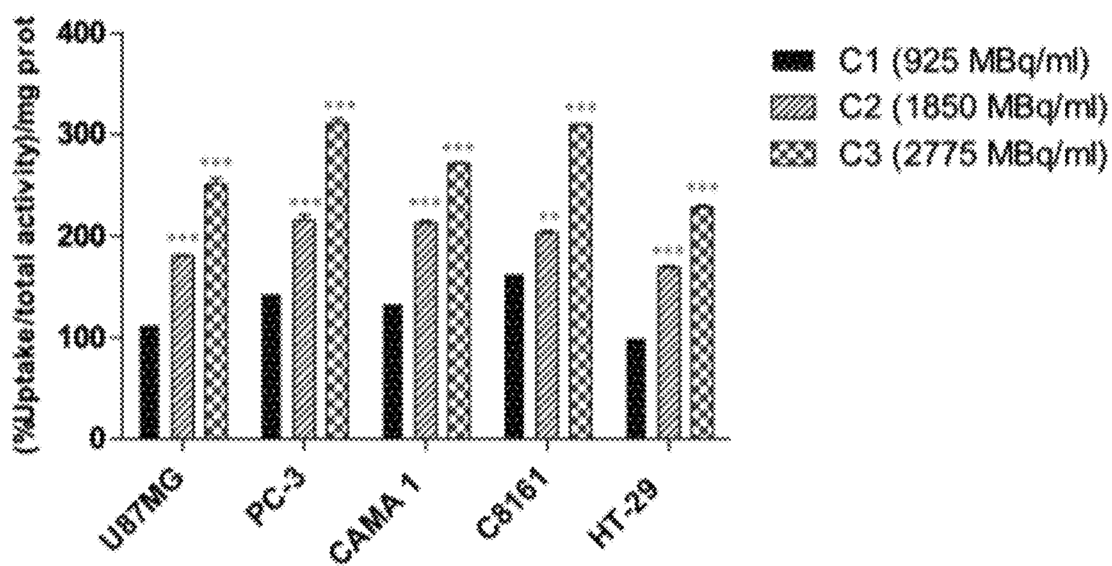
FIG. 1—Impact of different radioconcentrations on tumor cell uptake $^{64}CuCl_2$ cell uptake in different tumor cell lines U87MG, PC-3, CAMA1, C8161, HT-29. Cell uptake was evaluated treating cells at the same dosage (15 MBq/dish 100 mm), but at three different radioconcentrations C1=925 MBq/mL, C2=1,850 MBq/mL, C3=2,775 MBq/mL. Values are expressed as mean±SEM.
Figure 2:
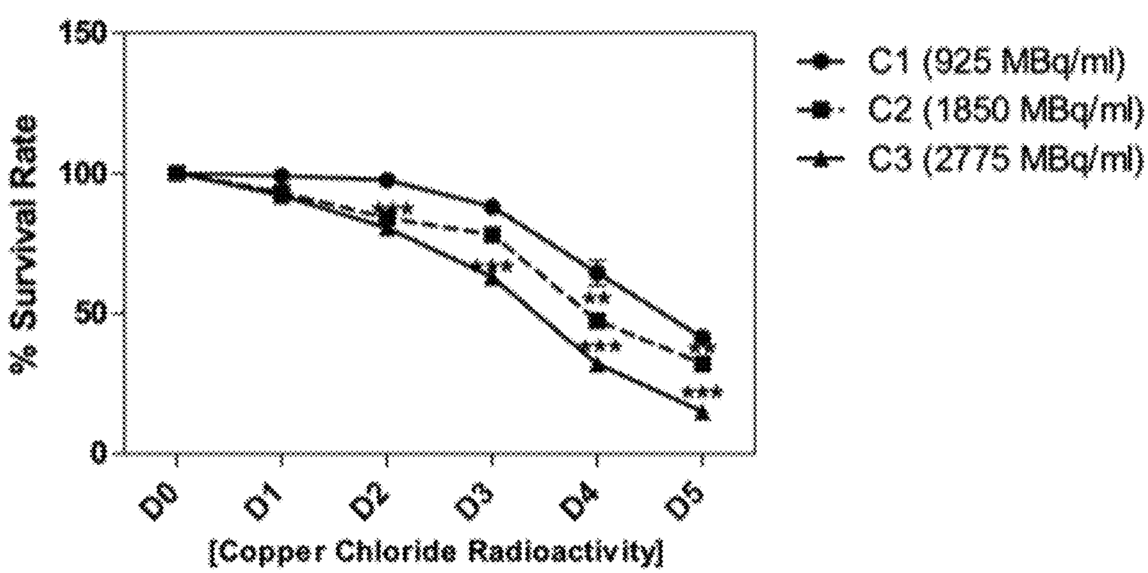
FIG. 2—Impact of different radioconcentrations on tumor cell survival
Figure 3:
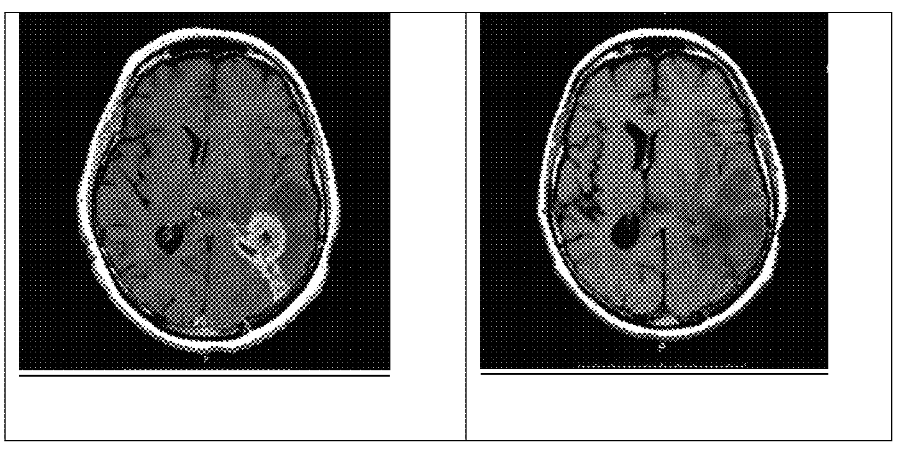
Figure 4:
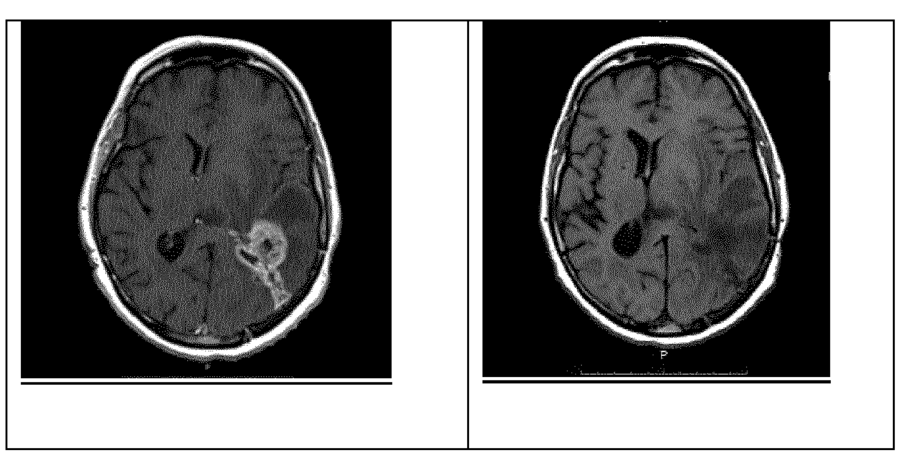

FIG. 3—Pre- and Post-treatment MRI

MRI of a glioblastoma patient treated with 7 fixed doses of 64CuCl2 (4,810 MBq) once a week.

On the left the MRI performed before starting treatment, on the right the MRI performed 90 days after the start of treatment. The patient resulted responder to the treatment indeed MRI showed a tumor volume reduction after treatment >50%.

EXAMPLES

Example 1—Compositions to be Used in the Selection Step

In the selection step an efficient amount of $^{64}CuCl_2$ is administered as a contrast agent for PET/CT or PET/MRI imaging. The composition of the medicinal product $^{64}CuCl_2$ for the selection step is a ready-to-use solution for injection (intravenous use) at a radioconcentration from 930 MBq/mL to 3,500 MBq/mL, preferably of 2,775 MBq/mL at date and time of calibration as a single dose product or as a multidose doses product. The volume of the solution for injection varies from 0.5 to 20 mL for single dose.

Drug synthesis steps are performed in a closed-system synthesis module which is automated and remotely controlled by GMP compliant software with automated monitoring and recording of the process parameters. In consideration of the nature of the product (radioactive) a natural decay of the radionuclide occurs, which is a property of radiopharmaceuticals, therefore the radio concentration change over time and this is the reason why the above mentioned raioconcentrations refers to a calibration time.

Example 2—Composition to be Used in the Treatment Step

The composition of the medicinal product $^{64}CuCl_2$ for the treatment step is a ready-to-use solution for injection (intravenous use) at a radioconcentration from 930 MBq/mL to 3,500 MBq/mL, at date and time of calibration as a single dose product or as a multidose doses product. The volume of the solution for injection varies from 0.5 to 20 mL for single dose. The solution can be diluted before administration with NaCl 0.9%.

Alternatively, the composition of the medicinal product $^{64}CuCl_2$ for the treatment step is a ready-to-use solution for infusion at a radioconcentration comprised between 50 MBq/mL and 925 MB/mL, at calibration time. The volume of the solution for infusion varies from 5 to 30 mL for single dose.

Drug synthesis steps are performed in a closed-system synthesis module which is automated and remotely controlled by GMP compliant software with automated monitoring and recording of the process parameters. In consideration of the nature of the product (radioactive) a natural decay of the radionuclide occurs, which is a property of radiopharmaceuticals, therefore the radio concentration change over time and this is the reason why the above mentioned radioconcentrations refers to a calibration time.

Example 3—Protocol for Treating a Human Patient with $^{64}CuCl_2$

In the present protocol the medicinal product used is $^{64}CuCl_2$ at a radioconcentration from 930 MBq/mL to 3,500 MBq/mL as solution for injection and as a single dose product. Copper-64 has a half-life of 12.7 hours.

Step a: Administering an Efficient Amount of $^{64}CuCl_2$ as a Contrast Agent for PET/CT or PET/MRI Imaging Patients with tumor received $^{64}CuCl_2$ at a dose between 370-925 MBq to ensure appropriate image quality. The mean effective dose for $^{64}CuCl_2$ calculated is 20 mSv per exam, which is aligned with the ones from the conventional PET imaging.

Step b: Acquiring Images PET/CT or PET/MRI Imaging With $^{64}CuCl_2$ and Selecting Patients for the Treatment The imaging PET/CT or PET/MRI is performed 1 h after $^{64}CuCl_2$ injection. In case an imaging PET/CT is acquired, the parameters for the CT (AC/AL): 100 mAs (adjustments will be possible according to body mass), 130 kVa, contiguous slices of 5 mm. Once the CT acquisition is completed, the PET acquisition includes 2 number of iterations, 8 number of subsets, 128 acquisition matrix. Each PET bad position is acquired for 3-4 minutes, providing a total scan time of 15-20 minutes. After performing the PET/CT or PET/MRI scan, the imaging is evaluated to identify lesions and see the uptake of $^{64}CuCl_2$ in the cancer lesion of the patient. $SUV_{max}$ of the lesion and the $SUV_{background}$ for the specific "background tissue" is measured to calculate the Target to background ratio (TBR). Patient's lesion is determined as positive for $^{64}CuCl_2$ uptake (i.e. evidencing an uptake of $^{64}CuCl_2$), if TBR results equal or higher than 5. In this case the subject, showing copper-64 uptake, is eligible and can proceed with treatment.

Step c: Treatment With $^{64}CuCl_2$

The treatment can start from the same day of the diagnostic administration up to 30 days after diagnostic administration. The patients identified with positive tumor lesions according to step b) receives a therapeutic dose in the range 1,850 MBq-4,810 MBq of $^{64}CuCl_2$ in 1-7 doses via parental administration.

According to nuclear medicine clinical practice a range of ±10% is accepted for each administered dose without any risk for the safety of the patient.

The treatment can be monitored during the course, the day of injection of the therapeutic dose a PET/CT or a PET/MRI can be acquired.

Example 4—Selection of Cancer Patients for the Treatment with TBR

According to the dosimetry evaluations from two different phase I clinical trials, evaluating the preliminary capability of $^{64}CuCl_2$ to be a theragnostic agent respectively in 16 patients affected by glioblastoma and 16 patients affected by prostate cancer, the TBR obtained from the PET/CT scan performed in the selection/eligibility step was also correlated to the response to copper chloride treatment. These results showed that the TBR of the non-responder patient was higher compared to the responder ones, in particular on the basis of the clinical data, TBR value >25 resulted in non-responder patients and TBR from 5 to 25 resulted in patients classified as responders. Therefore TBR, in addition to represent an index of tumor uptake in patients, it can be a predictive index of $^{64}CuCl_2$ treatment response. The PET/CT or PET/MRI results essential to select the proper patient that can start $^{64}CuCl_2$ treatment avoiding to expose the patient to the risk to start an unsuccessful treatment.

Example 5—Pharmacokinetic Profile of the Composition

Six glioblastoma patients were evaluated for safety profile and the study of biodistribution was conducted including evaluation of PET/CT scans after first daily dose administration of radiopharmaceutical composition having a radioconcentration of 2,775 MBq/mL (day 0), at different time points 1 h, 4 h, 24 h, 48 h after injection and pharmacokinetic (PK) radioactivity on blood samples at different time points of administration.

The $^{64}Cu$ pharmacokinetic profile in the present study showed that the $^{64}Cu$ uptake increases up to 4 h post-injection and decreased thereafter, indicating the *in vivo* stability of the theragnostic radiopharmaceutical. Data revealed a significant uptake in the liver (as expected) followed by kidney and L2-L4 regions. No treatment related toxicities were registered associated to liver/kidney and red marrow distribution. The effective dose ranged from 0.27 to 45.44 mSv with a median of 26.08 mSv. These values were considered acceptable for a theragnostic application.

Example 6—Response to $^{64}CuCl_2$ Treatment in Glioblastoma Patients

A glioblastoma patient of 70 kg that belongs to the class of recurrent glioblastoma. The patient underwent surgery, radiotherapy and chemotherapy and after that experienced recurrence. Standard treatment are not effective in this setting therefore the patient received a diagnostic dose of $^{64}CuCl_2$ equal to 925 MBq. After 1 h from administration a PET/CT scan is performed. The patient resulted positive for copper lesion at the diagnostic dose and started treatment The treatment with $^{64}CuCl_2$ (2,775 MBq/mL) for intravenous use by injection followed this scheme and the patient received once a week:

1st dose=4,810 MBq, 2nd dose=4,810 MBq, 3rd dose=4,810 MBq, 4th dose=4,810 MBq, 5th dose=4,810 MBq, 6th dose=4,810 MBq, 7th dose=4,810 MBq Where the total activity administered is equal to 33,670 MBq×cycle.

The radiopharmaceutical composition tested with this dosage regimen showed the capability to induce a tumor volume reduction. In particular, standard imaging (MRI) showed a tumor volume reduction after 3 months (day 90) from the treatment over 50% (FIG. 3).

Example 7—Treatment of a Prostate Cancer Patient that Belongs to the Class of Metastatic Prostate Cancer The patient at initial diagnosis had local tumor, and after surgery (radical prostatectomy) he underwent radiotherapy and chemotherapy. However, he experienced local recurrence plus a bone metastatic lesion. After receiving all standard treatments, the patient received a diagnostic dose of $^{64}CuCl_2$ equal to 925 MBq. After 1 h from administration a PET/CT scan is performed. The patient resulted positive for copper lesion at the diagnostic dose and started treatment.

The treatment with the composition $^{64}CuCl_2$ (2,775 MBq/mL) as solution for injection followed this scheme and the patient received once a week:

1st dose=4,810 MBq, 2nd dose=4,810 MBq, 3rd dose=4,810 MBq, 4th dose=4,810 MBq, 5th dose=4,810 MBq, 6th dose=4,810 MBq 7th dose=4,810 MBq Where the total activity administered is equal to 33,670 MBq×cycle.

After the treatment the analysis of the PET/CT before and after treatment showed a reduction of the tumor lesions on the bone, indicating a therapeutic effect of this composition.

Example 8—Treatment of a Glioblastoma Patient that Belongs to the Class of Recurrent Glioblastoma The patient (71 Kg) underwent surgery, radiotherapy and chemotherapy and after that experienced recurrence. Standard treatments are not effective in this setting therefore the patient received a diagnostic dose of $^{64}CuCl_2$ equal to 925 MBq. After 1 h from administration a PET/CT scan is performed. The patient resulted positive for copper lesion at the diagnostic dose and started treatment ($^{64}CuCl_2$ 277 MBq/mL for intravenous by infusion).

The treatment followed this scheme and the patient received once a week:

$1^{st}$ dose=1,850 MBq, $2^{nd}$ dose=2,460 MBq, $3^{rd}$ dose=2,922 MBq, $4^{th}$ dose=3,292 MBq, $5^{th}$ dose=3,606 MBq, $6^{th}$ dose=3,865 MBq, $7^{th}$ dose=4,068 MBq.

The total activity administered is equal to 22,063 MBq per cycle.

The patient resulted responder to the treatment.

Example 9—Treatment of a Paediatric Patient Affected by High Grade Glioma

The patient (25 kg) received a diagnostic dose of $^{64}CuCl_2$ equal to 132.5 MBq. After 1 h from administration a PET/CT scan is performed. The child resulted positive for copper lesion at the diagnostic dose and the treatment started.

The patient received the following treatment scheme with 3 treatments per week:

1st dose=1,700 MBq, 2nd dose=1,700 MBq, 3rd dose=1,700 MBq, 4th dose=1,700 MBq, 5th dose=1,700 MBq, 6th dose=1,700 MBq 7th dose=1,700 MBq Where the total activity administered is equal to 11,900 MBq×cycle.

The composition was $^{64}CuCl_2$ 925 MBq/mL for intravenous administration by infusion.

Example 10—Treatment Response after 7 Doses of $^{64}CuCl_2$

The phase I clinical trial on glioblastoma is the first study evaluating preliminary efficacy of $^{64}CuCl_2$ 2,775 MBq/mL as therapeutic agent. This determination was performed on 10 patients, at the end of the 7th therapy dose, at 90th day (after 3 months of the last treatment) and whenever possible at 180th day to obtain a wider evaluation of the disease status. Data cut-off was performed after 5 patients. The response to treatment, in term of anti-tumor activity of $^{64}CuCl_2$, was measured by MRI, assessed according to the RANO criteria (Response Assessment in Neuro-Oncology, see Wen P Y et al.) and defined as complete response (disappearance of tumor) partial response (reduction) and stable disease (non-progression of GBM). Among these patients 4 resulted responders and 1 non-responder. All patients were evaluated after 7 treatments with $^{64}CuCl_2$ and MRI assessment of the responder patients showed, at day 42 evaluation, stable disease in 3 patients and a reduction of tumor volume ≥50% compared to baseline MRI examination in one patient. Tumor volume reduction ≥50% was also shown in two cases after three months from the last treatment, and in one patient after 6 months from the last treatment. Furthermore 2 patients resulted at day 90 with stable disease and one showed stable disease up to six months after treatment.

Example 11—Monitoring to Response to Treatment

The PET/CT (or PET/MRI) can be used to monitor response to the treatment without the necessity to inject another tracer but acquiring the PET/CT after the administration. Infact in 10 patients affected by glioblastoma treated with 7 doses of $^{64}CuCl_2$ a PET/CT was acquired at the end of the 7$^{th}$ therapeutic doses. At the same timepoint a standard imaging, an MRI examination was performed. The response to treatment, in term of anti-tumor activity of $^{64}CuCl_2$, was measured by MRI, assessed according to the RANO criteria and defined as complete response (disappearance of tumor) partial response (reduction) and stable disease (non-progression of GBM). Two external revisors analyzed the PET/CT imaging for number of lesions, localization of lesion, SUVmax lesion, SUVbackground, TBR. The response to treatment was also measured by PET/CT. The analysis obtained with the standard imaging MRI were compared with the analysis obtained by PET/CT imaging, the results show coincidence in localization of tumor lesion and a superimposable classification of response to treatment, indicating the $^{64}CuCl_2$ PET/CT a technique useful to monitor the response to treatment over due course. This method can be applied to all the tumor lines that are able to have an uptake of Copper-64.

Example 12—Treatment Response after 4 Doses of $^{64}CuCl_2$

Five patients affected by prostate cancer showed treatment response after 4 injections of therapeutic administration of $^{64}CuCl_2$ 2,775 MBq/mL solution for injection. The PET/CT acquired the same day of the 4$^{th}$ therapeutic administration and the PET/CT acquired before treatment beginning were analyzed by two independent observers (a third observer expressed another evaluation only in case of discrepancies). After 4 administrations the volume of lesions showed a reduction or a non-progression indicating the efficacy of the treatment.

BIBLIOGRAPHY

Bai Y, Wang G, Fu W, Lu Y, Wei W, Chen W, Wu X, Meng H, Feng Y, Liu Y, Li G, Wang S, Wang K, Dai J, Li H, Li M, Huang J, Li Y, Wei S, Yuan J, Yao P, Miao X, He M, Zhang X, Yang H, Wu T, Guo H. Circulating essential metals and lung cancer: Risk assessment and potential molecular effects. Environ Int. 2019 June.; 127:685-693.

Ballinger J R. Theranostic radiopharmaceuticals: established agents in current use. Br J Radiol. 2018 November; 91(1091):20170969. doi: 10.1259/bjr.20170969. Epub 2018 Mar. 12. PMID: 29474096; PMCID: PMC6475961.

Beaino W, Guo Y, Chang A J, Anderson C J. Roles of Atox1 and p53 in the trafficking of copper-64 to tumor cell nuclei: implications for cancer therapy. J Biol Inorg Chem. 2014 March; 19(3):427-38.

Cai H, Wu J S, Muzik O, Hsieh J T, Lee R J, Peng F. Reduced 64Cu uptake and tumor growth inhibition by knockdown of human copper transporter 1 in xenograft mouse model of prostate cancer. J Nucl Med. 2014; 55: 622-8.

Capasso E., Durzu S., Piras S, et al. Role of 64CuCl2 PET/CT in staging of prostate cancer. Ann Nucl Med., 29:482-8, 2015;

Catalogna G., Talarico C. and Dattilo V. The SGK1 Kinase Inhibitor SI113 sensitizes theragnostic effects of the 64CuCl2 in human glioblastoma multiforme cells. Cellular Physiology and Biochemistry, 43:108-119, 2017.

Ferrari C., Asabella A N. And Villano C. Copper-64 dichloride as theragnostic agent for glioblastoma multiforme: a preclinical study. BioMed Research International, 2015.

Fisher G L, Shifrine M (1978) Hypothesis for the mechanism of elevated serum copper in cancer patients. Oncology 35: 22-25.

Fuchs A, Lustig E D. Localization of tissue copper in mouse mammary tumors. Oncology 1989; 46:183-7.

García-Pérez F O, Medina-Ornelas S S, Barron-Barron F, Arrieta-Rodriguez O. Evaluation of non-small cell lung cancer by PET/CT with 64CuCl2: initial experience in humans. Am J Nucl Med Mol Imaging. 2020 Jun. 15; 10(3):143-150. PMID: 32704405; PMCID: PMC7364381.

Guerreiro J F, Alves V, Abrunhosa A J, Paulo A, Gil O M, Mendes F. Radiobiological Characterization of $64CuCl_2$ as a Simple Tool for Prostate Cancer Theragnostics. Molecules. 2018 Nov. 11; 23(11):2944.

Karginova O, Weekley C M, Raoul A, Alsayed A, Wu T, Lee S S, He C, Olopade O I. Inhibition of Copper Transport Induces Apoptosis in Triple-Negative Breast Cancer Cells and Suppresses Tumor Angiogenesis. Mol Cancer Ther. 2019 May; 18(5):873-885. doi: 10.1158/1535-7163.MCT-18-0667. Epub 2019 Mar. 1. PMID:

Kim K I, Jang S J, Park J H, Lee Y J, Lee T S, Woo K S, et al. Detection of increased 64Cu uptake by human copper transporter 1 gene overexpression using PET with 64CuCl2 in human breast cancer xenograft model. J Nucl Med Off Publ Soc Nucl Med. 2014; 55:1692-8.

Howell R. W. Radiation spectra for Auger-electron emitting radionuclides: report No. 2 of AAPM NuclearMedicine Task Group No. 6. Med Phys. 1992 November-December; 19(6):1371-83.

Hu G F. Copper stimulates proliferation of human endothelial cells under culture. J Cell Biochem. 1998 Jun. 1; 69(3):326-35.

Lapa C. Exciting Opportunities in Nuclear Medicine Imaging and Therapy. J Clin Med. 2019 Nov. 12; 8(11):1944. doi: 10.3390/jcm8111944. PMID: 31718092; PMCID: PMC6912644.

Lelièvre P, Sancey L, Coll J L, Deniaud A, Busser B. The Multifaceted Roles of Copper in Cancer: A Trace Metal Element with Dysregulated Metabolism, but Also a Target or a Bullet for Therapy. Cancers (Basel). 2020 Dec. 1; 12(12):3594. doi: 10.3390/cancers12123594. PMID: 33271772; PMCID: PMC7760327.

Manjula S, Aroor A R, Raja A, Rao S N, Rao A. Elevation of serum ceruloplasmin levels in brain tumours. Acta Neurol Scand. 1992 August; 86(2):156-8. doi: 10.1111/j.1600-0404.1992.tb05058.x. PMID: 1414225.

Pamar et al. 2018"In vivo [64Cu]CuCl2 PET imaging reveals activity of Dextran-Catechin on tumor copper homeostasis"

Panichelli P, Villano C, Cistaro A, Bruno A, Barbato F, Piccardo A, Duatti A. Imaging of Brain Tumors with Copper-64 Chloride: Early Experience and Results. Cancer Biother Radiopharm. 2016 June; 31(5):159-67.

Peng F, Liu J, Wu J S, Lu X, Muzik O. Mouse extrahepatic hepatoma detected on MicroPET using copper (II)-64 chloride uptake mediated by endogenous mouse copper transporter 1. Mol Imaging Biol. 2005 September-October; 7(5):325-9.

Peng F., Lu X. and Janisse J. PET of human prostate cancer xenografts mice with increased uptake of 64CuCl2. The jurnal of nuclear medicine, Vol 47 n° 10 pp 1649-1652, 2006.

Piccardo A, Paparo F, Puntoni M, Righi S, Bottoni G, Bacigalupo L, Zanardi S, DeCensi A, Ferrarazzo G, Gambaro M, Ruggieri F G, Campodonico F, Tomasello L, Timossi L, Sola S, Lopci E, Cabria M. 64CuCl2 PET/CT in Prostate Cancer Relapse. J Nucl Med. 2018 March; 59(3):444-451. doi: 10.2967/jnumed.117.195628. Epub 2017 Sep. 8. PMID: 28887398. Pinto CIG, Bucar S, Alves V, Fonseca A, Abrunhosa A J, da Silva C L, Guerreiro J F, Mendes F. Copper-64 Chloride Exhibits Therapeutic Potential in Three-Dimensional Cellular Models of Prostate Cancer. Front Mol Biosci. 2020 Dec. 1; 7:609172. doi: 10.3389/fmolb.2020.609172. PMID: 33335914; PMCID: PMC7736412.

Qin C, Liu H, Chen K, Hu X, Ma X, Lan X, Zhang Y, Cheng Z. Theragnostics of malignant melanoma with 64CuCl2. J Nucl Med. 2014 May; 55(5):812-7. doi: 10.2967/jnumed.113.133850. Epub 2014 Mar. 13. PMID: 24627435; PMCID: PMC4346241.

Saleh S, A, K, Adly H, M, Abdelkhaliq A, A, Nassir A, M: Serum Levels of Selenium, Zinc, Copper, Manganese, and Iron in Prostate Cancer Patients. Curr Urol 2020; 14:44-49. doi: 10.1159/000499261

Scanni A, Tomirotti M, Licciardello L, Annibali E, Biraghi M, Trovato M, Fittipaldi M, Adamoli P, Curtarello G (1979) Variations in serum copper and ceruloplasmin levels in advanced gastrointestinal cancer treated with polychemotherapy. Tumori 65:331 338.

Wang Q, Song D, Ma X, Wu X, Jiang L. Preclinical PET imaging study of lung cancer with 64CuCl2. Ann Nucl Med. 2020 September; 34(9):653-662. doi: 10.1007/s12149-020-01491-6. Epub 2020 Jun. 21. PMID: 32567008.

Wen P Y, Chang S M, Van den Bent M J, Vogelbaum M A, Macdonald D R, Lee E Q. Response Assessment in Neuro-Oncology Clinical Trials. J Clin Oncol. 2017 Jul. 20; 35(21):2439-2449.

Zhang M, Shi M, Zhao Y. Association between serum copper levels and cervical cancer risk: a meta-analysis. Biosci Rep. 2018; 38(4):BSR20180161. Published 2018 Jul. 6.

The invention claimed is:

1. A method of treating a patient suffering from a neoplasm, said method comprising a treatment cycle comprising administering to said patient a radiopharmaceutical composition comprising as the active ingredient $^{64}Cu^{++}$, in combination with suitable excipients and/or diluents in a saline solution, having a radioconcentration higher than 925 MBq/mL up to 3,500 MBq/mL at calibration time, wherein the radiopharmaceutical composition is administered at a dose from 7 MBq/kg to 210 MBq/kg.

2. The method of treatment according to claim 1, wherein the method is preceded by a step for evaluating eligibility of the patient for the treatment comprising determining the copper level in a blood sample of the patient and said eligibility is established only if serum copper level detected in a blood sample of the patient is over 60 μg/dL.

3. The method of treatment according to claim 1, wherein the method is preceded by a step for evaluating eligibility of the patient for the treatment comprising performing PET/MRI or PET/CT scan on said patient to confirm copper-$64^{++}$ uptake by the neoplasm.

4. The method of treatment according to claim 3, wherein the evaluating step is performed by a computer.

5. The method of treatment according to claim 1, wherein the treatment is followed by a step for monitoring the response of the patient to the treatment, where the same radiopharmaceutical composition of claim 1 is administered to perform PET/CT or PET/MRI scan on said patient.

6. A method of treating a patient suffering from a neoplasm, said method comprising administering to said patient a radiopharmaceutical composition comprising as the active ingredient $^{64}Cu^{++}$, in combination with suitable excipients and/or diluents in a saline solution, having a radioconcentration comprised between 50 and 3,500 MBq/mL, at calibration time, wherein radiopharmaceutical composition is administered to said patient at a dose from 7 MBq/kg to 210 MBq/kg and wherein the administration is intravenous by infusion.

7. The method of treatment according to claim 1, wherein the radioconcentration at calibration time is comprised between 1,850 MBq/mL and 2,775 MBq/mL.

8. The method of treatment according to claim 6, wherein the method is preceded by a step for evaluating of the eligibility of the patient for the treatment comprising determining the copper level in a blood sample of the patient and said eligibility is established only if serum copper level detected in a blood sample of the patient is over 60 μg/dL.

9. The method of treatment according to claim 6, wherein the treatment is followed by a phase of monitoring the response of the patient to the treatment, where the same radiopharmaceutical composition of claim 6 is administered to perform PET/CT or PET/MRI scan on said patient.

10. The method of treatment according to claim 1, wherein the neoplasm is selected from the group consisting of a benign neoplasm, an in situ neoplasm, a malignant neoplasm or head-neck cancer, brain cancer, glioma, glioblastoma, astrocytoma, prostate cancer, metastatic prostate cancer, breast cancer, ovary cancer, lung cancer, lymphoma and melanoma.

11. The method of treatment according to claim 6, wherein the neoplasm is selected from the group consisting of a benign neoplasm, an in situ neoplasm, a malignant neoplasm or head-neck cancer, brain cancer, glioma, glioblastoma, astrocytoma, prostate cancer, metastatic prostate cancer, breast cancer, ovary cancer, lung cancer, lymphoma and melanoma.

12. The method of treatment according to claim 1, wherein the composition is administered by intramuscular, intradermal, subcutaneous, intratumoral, intracavity, intrathecal or intravenous route and intravenously by injection.

13. The method of treatment according to claim 6, wherein the radioconcentration at calibration time is equal to 925 MBq/mL.

14. The method of treatment according to claim 3, wherein the determination of the $^{64}Cu^{++}$ uptake by the neoplastic cells is carried out by measuring the target to background ratio (TBR) value through PET imaging, where a TBR value equal or higher than 5 is considered as evidencing an uptake of $^{64}Cu^{++}$ by the neoplastic cells.

15. The method of treatment according to claim 3, wherein the evaluating step comprises administering radiopharmaceutical composition comprising as the active ingredient $^{64}Cu^{++}$ at a dose between 3 MBq/kg and 14 MBq/kg.

16. The method of treatment according to claim 6, wherein the method is preceded by a step for evaluating eligibility of the patient for the treatment comprising performing PET/MRI or PET/CT scan of said patient to confirm copper-$64^{++}$ uptake by the neoplasm.

17. The method of treatment according to claim 16, wherein the radiopharmaceutical composition is administered at a dose between 3 MBq/kg and 14 MBq/kg to evaluate the eligibility of the patient for the treatment.

18. The method of treatment according to claim 1, wherein the administering step is repeated for 1 to 7 times per each cycle, each cycle is repeated from one to seven times and the frequency of comprises from 1 to 3 administrations per week.

19. The method of treatment according to claim 6, wherein the administering step is repeated for 1 to 7 times per each cycle, each cycle is repeated from one to seven times and the frequency of administration per each cycle comprises from 1 to 3 administrations per week.

20. The method of treatment according to claim 1, wherein for each treatment cycle the dosage regimen is at an increasing dose starting from the initial therapeutic dose (X1 MBq) as indicated in the following scheme:

| | |
|---|---|
| 1st dose | X1 MBq |
| 2nd dose | X2 = (X1 + 33% of X1) MBq |
| 3rd dose | X3 = (X2 + 25% of X1) MBq |
| 4th dose | X4 = (X3 + 20% of X1) MBq |
| 5th dose | X5 = (X4 + 17% of X1) MBq |
| 6th dose | X6 = (X5 + 14% of X1) MBq |
| 7th dose | X7 = (X6 + 11% of X1) MBq |

or at a fixed dose of the radiopharmaceutical composition.

21. The method of treatment according to claim 1, wherein for each treatment cycle the dosage regimen comprises the following doses for an adult patient: 1st dose=1,850 MBq, 2nd dose=2,460MBq, 3rd dose=2,922 MBq, 4th dose=3,292 MBq, 5th dose=3,606 MBq, 6th dose=3,865 MBq, 7th dose=4,068 MBq, where the total dosage is equal to 22,063 MBq per cycle.

22. The method of treatment according to claim 1, wherein for each treatment cycle the dosage regimen comprises the following doses for an adult patient: 1st dose=4,810 MBq, 2nd dose=4,810 MBq, 3rd dose=4,810 MBq, 4th dose=4,810 MBq, 5th dose=4,810 MBq, 6th dose=4,810MBq, 7th dose=4,810MBq, where the total dosage activity is equal to 33,670 MBq per cycle.

23. The method of treatment according to claim 6, wherein for each treatment cycle the dosage regimen comprises the following doses for a pediatric patient 1st dose=1,700 MBq, 2nd dose=1,700 MBq, 3rd dose=1,700 MBq, 4th dose=1,700 MBq, 5th dose=1,700 MBq, 6th dose=1,700 MBq 7th dose=1,700 MBq, where the total dosage administered is equal to 11,900 MBq×cycle.

* * * * *